(12) United States Patent
Davis

(10) Patent No.: US 11,097,995 B1
(45) Date of Patent: Aug. 24, 2021

(54) FUEL PRODUCTION FROM ALCOHOLS

(71) Applicant: The United States of America, as represented by the Secretary of the Navy, Arlington, VA (US)

(72) Inventor: Matthew C. Davis, Ridgecrest, CA (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 16/876,338

(22) Filed: May 18, 2020

Related U.S. Application Data

(60) Provisional application No. 62/879,827, filed on Jul. 29, 2019.

(51) Int. Cl.
*C07C 1/24* (2006.01)
*C07C 1/04* (2006.01)
(Continued)

(52) U.S. Cl.
CPC .............. *C07C 1/24* (2013.01); *C07C 1/045* (2013.01); *C07C 5/03* (2013.01); *C07C 7/06* (2013.01);
(Continued)

(58) Field of Classification Search
CPC .. C07C 1/045; C07C 1/24; C07C 5/03; C07C 7/06; C07C 11/02; C07C 2523/42;
(Continued)

(56) References Cited

U.S. PATENT DOCUMENTS

| | | | |
|---|---|---|---|
| 9,758,737 B1* | 9/2017 | Harvey | C07C 5/29 |
| 2004/0006252 A1* | 1/2004 | Smith, Jr. | C07C 2/28 |
| | | | 585/639 |

(Continued)

*Primary Examiner* — Youngsul Jeong
*Assistant Examiner* — Jason Y Chong
(74) *Attorney, Agent, or Firm* — Naval Air Warfare Center Weapons Division; Matthew D. Pangallo; Stuart H Nissim

(57) ABSTRACT

A method of making fuel including adding alcohol to a reactor with a zinc dihalide salt and heating the reactor to reflux, thereby forming a mixture. Water is removed from the mixture using azeotropic distillation. The mixture is distilled, thereby forming oligo(alkenes)$_n$ and residual alcohol. The oligo(alkenes)$_n$ are distilled using fractionation, thereby forming a first, a second, a third fraction, and removing the residual alcohol. The first fraction includes oligo(alkenes)$_n$ with n ranging from 2 to 4, the second fraction includes oligo(alkenes)$_n$ with n ranging from 4 to 8, and the third fraction includes oligo(alkenes)$_n$ with n ranging from 8 to 12. The first, second, and third fractions are hydrogenated, thereby forming oligo(alkanes)$_n$. The first fraction includes oligo(alkanes)$_n$ with n ranging from 2 to 4, the second fraction includes oligo(alkanes)$_n$ with n ranging from 4 to 8, and the third fraction includes oligo(alkanes)$_n$ with n ranging from 8 to 12.

15 Claims, 4 Drawing Sheets

(51) Int. Cl.
*C07C 7/06* (2006.01)
*C07C 5/03* (2006.01)
C07C 11/02 (2006.01)
C07C 9/14 (2006.01)
C07C 9/10 (2006.01)
C07C 9/08 (2006.01)
C07C 9/06 (2006.01)

(52) U.S. Cl.
CPC .................. *C07C 9/06* (2013.01); *C07C 9/08* (2013.01); *C07C 9/10* (2013.01); *C07C 9/14* (2013.01); *C07C 11/02* (2013.01); *C07C 2523/42* (2013.01); *C07C 2523/44* (2013.01); *C07C 2523/46* (2013.01); *C07C 2523/755* (2013.01); *C07C 2527/138* (2013.01)

(58) Field of Classification Search
CPC ............ C07C 2523/44; C07C 2523/46; C07C 2523/755; C07C 2527/138
See application file for complete search history.

(56) References Cited

U.S. PATENT DOCUMENTS

2011/0288352 A1* 11/2011 Peters ...................... C10G 3/44
585/14
2016/0076062 A1* 3/2016 Medoff .................... C08K 3/04
562/589
2017/0349529 A1* 12/2017 Crockatt ............... C07C 67/347

* cited by examiner

FUEL PRODUCTION FROM ALCOHOLS

CROSS-REFERENCE TO RELATED APPLICATION

This is a non-provisional patent application claiming priority to the provisional patent application 62/879,827 filed on Jul. 29, 2019. The entire disclosure of patent application 62/879,827 is incorporated herein by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND

Fuel precursors can be chemically produced from petroleum and bio-based sources or obtained from naturally occurring crude oil sources. When producing fuel from crude oil sources, a complex mixture of hydrocarbons is added to a distillation column with a temperature gradient to separate the molecules based on their molecular weight and volatility. Isolation of a well-defined distillation cut allows for the production of various fuel blends with properties suitable for use in specific applications. For example, jet fuel may contain a mixture of hydrocarbons having between 9 to 14 carbon atoms in each molecule.

BRIEF DESCRIPTION OF THE DRAWINGS

Features and advantages of examples of the present disclosure will be apparent by reference to the following detailed description and drawings, in which like reference numerals correspond to similar, but in some instances, not identical, components. Reference numerals or features having a previously described function may or may not be described in connection with other drawings in which they appear.

DETAILED DESCRIPTION

Ethanol is produced in large volumes every year by the process known as fermentation. During ethanol production, a small volume of fusel oil is produced by the Ehrlich degradation pathway of certain amino acids. At mass-production scale, the small volume of fusel oil byproduct can be produced in large volumes, which can become a monetarily significant product stream. Fusel oil is a mixture of different higher aliphatic alcohols (>C2) based on the vegetable 'mash' and microorganisms employed in the fermentation. For example, the components of highest concentration in North American fusel oil are isoamyl alcohol (3-methyl-1-butanol) and 2-methyl-1-butanol. In general, reacting alcohols or a mixture of alcohols (e.g., fusel oil) with mineral acids or other acidic catalyst will yield products containing oxygen such as ethers, acetals, esters, and carbonate esters. As a result, these products cannot be hydrogenated to produce oxygen-free fuel without taking additional chemical processing steps to remove the oxygen. Currently, there is no process that efficiently and economically produces oxygen-free fuel from fusel oil or other mixtures of alcohols.

In the method herein, a zinc dihalide salt is reacted with the aliphatic alcohols (e.g., fusel oil) to produce oligo (alkenes)$_n$ that do not contain oxygen. Without the presence of oxygen, the oligo(alkenes)$_n$ can be hydrogenated to produce oligo(alkanes)$_n$. The oligo(alkanes)$_n$ can be separated by the length of the carbon chains to produce different types of fuel (e.g., jet fuel, diesel fuel, gasoline) or lubricant that can be blended with different types of conventional fuel (e.g., JP-8, JP-5, etc.) or conventional lubricants. As a result, fusel oil and other aliphatic alcohols can be efficiently and economically converted to hydrocarbons that form fuels or lubricants.

The method herein includes adding an alcohol to a reactor with a zinc dihalide salt and heating the reactor to reflux, thereby forming a mixture. Water is removed from the mixture using azeotropic distillation. The mixture is distilled, thereby forming oligo(alkenes)$_n$ and residual alcohol, where n ranges from 2 to 12. The oligo(alkenes)$_n$ are distilled with fractionation, thereby forming a first fraction, a second fraction, a third fraction, and removing the residual alcohol. The first fraction includes oligo(alkenes)$_n$ with n ranging from 2 to 4, the second fraction includes oligo (alkenes)$_n$ with n ranging from 4 to 8, and the third fraction includes oligo(alkenes)$_n$ with n ranging from 8 to 12. The first, second, and third fractions are hydrogenated, thereby forming oligo(alkanes)$_n$. The first fraction includes oligo (alkanes)$_n$ with n ranging from 2 to 4, the second fraction includes oligo(alkanes)$_n$ with n ranging from 4 to 8, and the third fraction includes oligo(alkanes)$_n$ with n ranging from 8 to 12.

Figure 1:
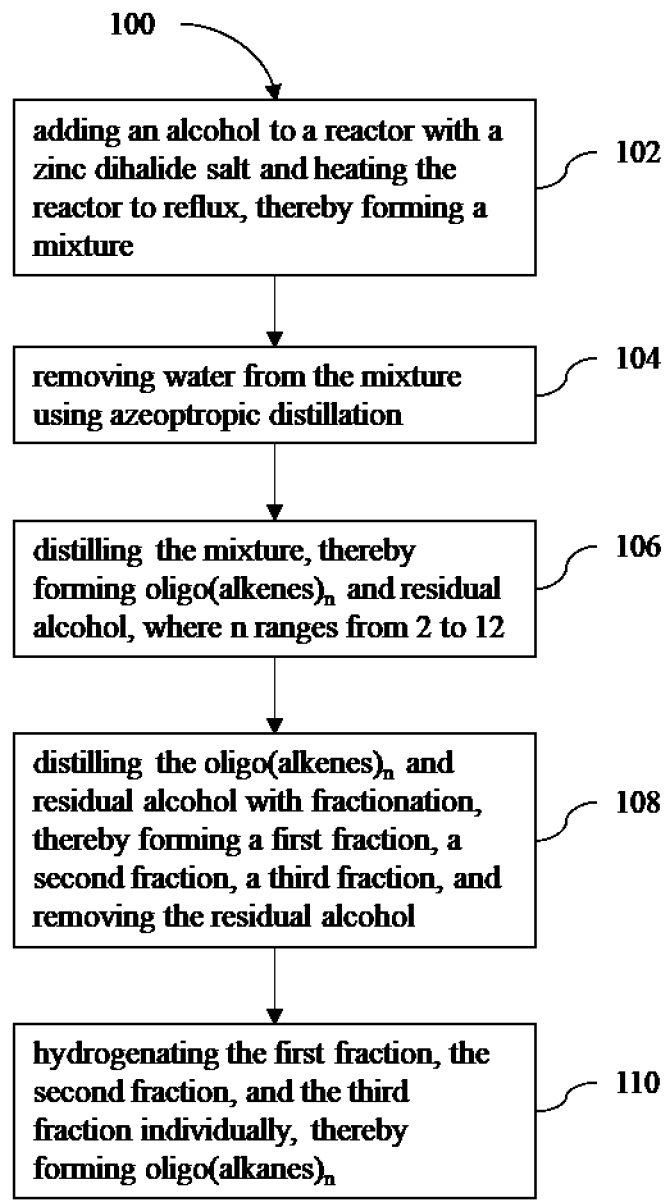
FIG. 1 is a flow diagram illustrating an example of a method for making a fuel described herein.
Figure 2:
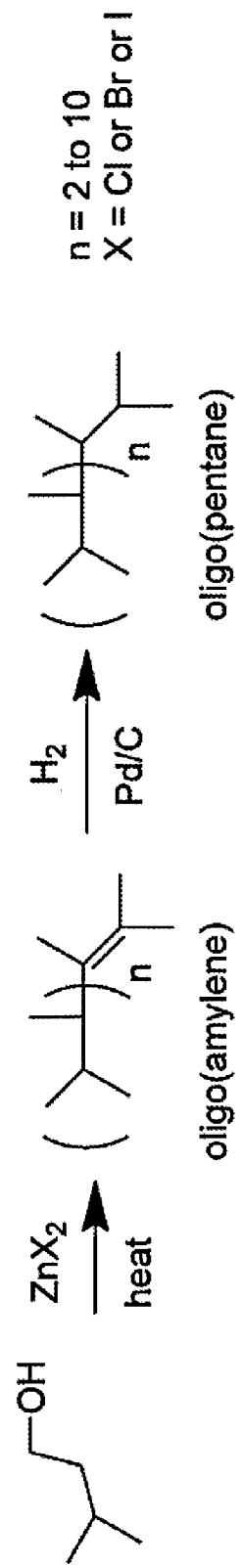
FIG. 2 is a scheme illustrating an example of a method for making a fuel described herein.

Referring now to FIG. 1, step 102 of the method 100 of making fuel includes adding an alcohol to a reactor with zinc dihalide salt and heating the reactor to reflux, thereby forming a mixture. This step is performed as the first step to deoxygenate carbon molecules within the mixture. The reactor is heated to a temperature ranging from about 100° C. to about 150° C. for a time ranging from about 2 hours to about 24 hours. The reactor may be any chemical reactor that can facilitate the reaction. For example, a borosilicate flask or glass-lined stainless steel reactor. An example of the synthesis of step 102 is shown in FIG. 2 where an alcohol is reacted with zinc dichloride, zinc dibromide, or zinc diiodide with heat to form oligo(amylene)$_n$.

The zinc dihalide salt facilitates removing the oxygen from the mixture. The zinc dihalide salt is present in a ratio of alcohol to zinc dihalide salt of about 1:1 to about 5:1. In some examples, the ratio of alcohol to zinc dihalide salt is 2:1. Additionally, the zinc dihalide salts can be recovered from the reaction and reused in subsequent reactions. In some examples, the zinc dihalide salts can be reused in at least four subsequent reactions without any reduction in the yield of the fuel. Some examples of the zinc dihalide salt include $ZnCl_2$, $ZnBr_2$, $ZnI_2$, Zn ditriflate, and combinations thereof.

The alcohol may be a single type of alcohol or a mixture of two or more alcohols. In an example, fusel oil may be used to react with the zinc dihalide salt. In another example, the alcohol is an aliphatic alcohol with the number of carbons ranging from 3 carbons to 6 carbons. Some specific examples of the alcohol include ethanol, isomers of propanol (1-propanol, 2-propanol), isomers of butanol (1-butanol, 2-butanol, 1,1-dimethyl-ethanol, 2-methyl-1-propanol), isomers of pentanol (3-methyl-2-butanol, 2-methyl-2-butanol, 3-methyl-1-butanol, 2-methyl-1-butanol, 2,2-dimethyl-1-propanol) and isomers of hexanol (hexan-1-ol, hexan-2-ol, hexan-3-ol, 2-methylpentan-1-ol, 3-methylpentan-1-ol, 4-methylpentan-1-ol, 2-methylpentan-2-ol, 3-methylpentan-2-ol, 4-methylpentan-2-ol, 2-methylpentan-3-ol, 3-methylpentan-3-ol, 2,2-dimethylbutan-1-ol, 2,3-dimethylbutan-1-ol, 3,3-dimethylbutan-1-ol, 2,3-dimethylbutan-2-ol, 3,3-dimethylbutan-2-ol, 2-ethylbutan-1-ol), and combinations thereof.

Referring to FIG. 1, step 104 of method 100 includes removing water from the mixture using azeotropic distillation. The azeotropic distillation uses a condensing trap, such as using a Dean-Stark trap, to separate the water from the mixture. The mixture is heated to a temperature ranging from about 80° C. to about 150° C. for a time ranging from about 1 hour to about 24 hours.

Referring to FIG. 1, step 106 of method 100 includes distilling the mixture, thereby forming oligo(alkenes)$_n$ and residual alcohol, where n ranges from 2 to 12. This step 106 forms a mixture of alkenes that can be more easily converted to fuel via hydrogenation. In this step 106, the distillation occurs at a reduced pressure ranging from about 0.1 torr to about 60 torr. The distillation occurs at a temperature ranging from about 80° C. to about 150° C.

There are a variety of oligo(alkenes)$_n$ that may be produced in step 106. Some specific examples of the oligo(alkenes)$_n$ produced include an alkene where n=2 can be 2,3,6-trimethylhept-2-ene and isomers thereof an alkene where n=3 can be 5-isopropyl-2,3,8-trimethylnon-2-ene and isomers thereof; an alkene where n=4 can be 5,7-diisopropyl-2,3,10-trimethylundec-2-ene and isomers thereof; an alkene where n=5 can be 5,7,9-triisopropyl-2,3,12-trimethyltridec-2-ene and isomers thereof; an alkene where n=8 can be 5,7,9,11,13,15-hexaisopropyl-2,3,18-trimethylnonadec-2-ene and isomers thereof or a combination of any of the above oligo(alkenes)$_n$. The oligo(alkenes)$_n$ produced in step 106 are not limited to the examples listed above.

Referring to FIG. 1, step 108 includes distilling the oligo(alkenes)$_n$ using fractionation, thereby forming a first fraction, a second fraction, a third fraction, and removing the residual alcohol. In step 108, the distilling occurs at a pressure ranging from about 0.1 torr to about 60 torr at temperatures ranging from about 80° C. to about 150° C. The first fraction includes oligo(alkenes)$_n$ with n ranging from 2 to 4. The second fraction includes oligo(alkenes)$_n$ with n ranging from 4 to 8. The third fraction includes oligo(alkenes)$_n$ with n ranging from 8 to 12. This step 108 allows each alkene to be separated not only by the length of the alkene, but also for the intended use of the fuel each fraction will produce. This is described in greater detail in step 110. Step 108 produces the oligo(alkenes)$_n$ in a yield of about 25%. In FIG. 2, an example of this synthesis is shown where the oligo(alkene)$_n$ is oligo(amylene)$_n$ where n ranges from 2 to 12. The residual alcohol is removed from the mixture by any known means. For example, fractionation may be used to separate the residual alcohol from the other oligo(alkenes)$_n$.

In step 108, the oligo(alkene)$_n$ formed is the same oligo(alkene)$_n$ as previously mentioned herein. For example, in the first fraction, the oligo(alkenes)$_n$ where n=2 to 4 can be 2,3,6-trimethylhept-2-ene and isomers thereof, 5-isopropyl-2,3,8-trimethylnon-2-ene and isomers thereof, 5,7-diisopropyl-2,3,10-trimethylundec-2-ene and isomers thereof, or a combination thereof. In the second fraction, the oligo(alkenes)$_n$ where n=4 to 8 can be 5,7-diisopropyl-2,3,10-trimethylundec-2-ene and isomers thereof, 5,7,9-triisopropyl-2,3,12-trimethyltridec-2-ene and isomers thereof, 5,7,9,11,13,15-hexaisopropyl-2,3,18-trimethylnonadec-2-ene and isomers thereof, or a combination thereof. In the third fraction, the oligo(alkenes)$_n$ where n=8 to 12 can be 5,7,9,11,13,15-hexaisopropyl-2,3,18-trimethylnonadec-2-ene and isomers thereof or a combination of oligo(alkenes)$_n$ where n=8 to 12. The oligo(alkenes)$_n$ produced in step 108 for the first fraction, the second fraction, and the third fraction are not limited to the examples listed above.

Referring to FIG. 1, step 110 includes hydrogenating the first, second, and third fractions individually, thereby forming oligo(alkanes)$_n$. The first fraction includes oligo(alkanes) with n ranging from 2 to 4. The second fraction includes oligo(alkanes)$_n$ with n ranging from 4 to 8. The third fraction includes oligo(alkanes)$_n$ with n ranging from 8 to 12. Each fraction contains a fuel that may be used for a specific purpose. For example, the first and second fractions may be used as a jet fuel blend while the third fraction may be used as a lubricant. FIG. 2 shows an example of the synthesis where the product produced is oligo(pentane)$_n$ where n ranges from 2 to 10.

There are a variety of oligo(alkanes)$_n$ that may be produced in step 110. Some specific examples of the oligo(alkanes)$_n$ produced include an alkane where n=2 can be 2,3,6-trimethylheptane and isomers thereof an alkane where n=3 can be 5-isopropyl-2,3,8-trimethylnonane and isomers thereof an alkane where n=4 can be 5,7-diisopropyl-2,3,10-trimethylundecane and isomers thereof an alkane where n=5 can be 5,7,9-triisopropyl-2,3,12-trimethyltridecane and isomers thereof an alkane where n=8 can be 5,7,9,11,13,15-hexaisopropyl-2,3,18-trimethylnonadecane and isomers thereof. The oligo(alkanes)$_n$ produced in step 110 are not limited to the examples listed above.

The hydrogenation occurs at a temperature ranging from about 20° C. to about 200° C. for a time ranging from about 1 hour to about 24 hours in a hydrogen atmosphere. The hydrogenation occurs at a pressure ranging from about 40 psi to about 1000 psi. The hydrogenation includes a catalyst selected from the group consisting of Ni, Pd, Pt, Ru, or combinations thereof. Since each fraction is separated from each other, each fraction has to be hydrogenated individually to create the fuel in each fraction.

The first fraction contains oligo(alkanes)$_n$ where n ranges from 2 to 4. This fraction can form a fuel blendstock in jet fuel or vehicle fuel. The fuel blendstock may be blended with a second fuel selected from the group consisting of JP-8, JP-5, Jet-A, Jet-A1, F-24, Diesel #2, F-76, gasoline and combinations thereof. The oligo(alkanes)$_n$ where n ranges from 2 to 4 may be present in the fuel blendstock in an amount ranging from 1% v/v to 50% v/v based on the total volume of the fuel blendstock.

Similarly, the second fraction, which contains oligo(alkanes)$_n$ where n ranges from 4 to 8, can also be used as a fuel blendstock in jet fuel or vehicle fuel. The fuel blendstock of the second fraction fuel may be blended with a second fuel selected from the group consisting of JP-8, JP-5, Jet-A, Jet-A1, F-24, Diesel #2, F-76, gasoline and combinations thereof. The oligo(alkanes)$_n$ where n ranges from 4 to 8 may be present in the fuel blendstock in an amount ranging from 1% v/v to 50% v/v based on the total volume of the fuel blendstock.

The third fraction contains oligo(alkanes)$_n$ where n ranges from 8 to 12. This fraction can form a lubricant blendstock. The lubricant blendstock in the third fraction may be blended with lubricants selected from the group consisting of motor oils, soap thickening greases, and hydraulic fluid.

The oligo(alkanes)$_n$ where n ranges from 8 to 12 may be present in a lubricant blendstock in an amount ranging from about 1% v/v to about 80% v/v based on the total v/v of the lubricant blendstock.

To further illustrate the present disclosure, examples are given herein. It is to be understood that these examples are provided for illustrative purposes and are not to be construed as limiting the scope of the present disclosure.

EXAMPLES

Example 1: Oligo(amylene)$_n$ Production

A round-bottomed flask (1 L) equipped with magnetic stirring bar was filled with crude fusel oil (287.5 g) containing approximately 15 wt % water. Next, anhydrous zinc dibromide (320 g, 1.42 mole) was added into the flask. A Dean-Stark trap and reflux condenser were attached to the flask and then the mixture was heated by an electric heating mantle controlled by a rheostat set at 55%. The mixture was refluxed and the water azeotrope became separated in the Dean-Stark trap. After 7 hours, a total of 85 mL of water had been collected in the trap. The mixture was cooled down to room temperature and a reduced pressure distillation head was equipped and the mixture was distilled at 11 torr and the rheostat set to 40% to collect 135 g of a colorless liquid product mixture. The distillation pot contained the zinc dibromide along with a residual higher boiling liquid of higher molecular weight oligo(amylene)$_n$ (n>12). The 135 g of crude product was distilled at reduced pressure (11 torr) a second time but with fractionation to separate the residual fusel alcohols from the oligo(amylene)$_n$ (n=2-12). The oligo(amylene)$_n$ weighed 50 grams, which is about a 25% yield.

Figure 3:
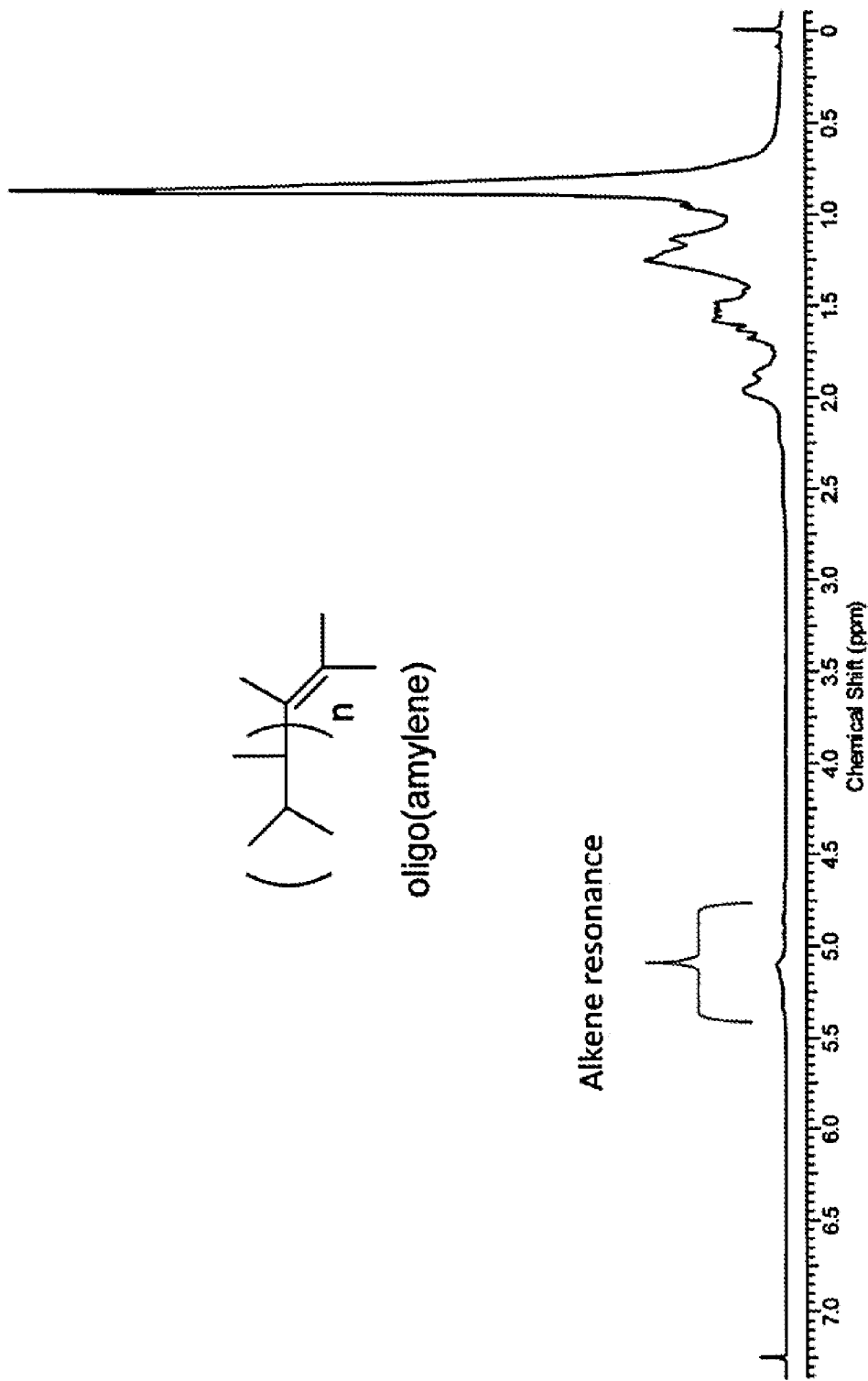
FIG. 3 is a $^1$H NMR spectrum of oligo(amylene)$_n$ produced in the method described herein.

A $^1$H NMR analysis was performed on the oligo(amylene)$_n$ dissolved in deuterochloroform. The results are shown for in FIG. 3 as a $^1$H NMR spectrum at 400 MHz. An elemental analysis was calculated for the oligo(amylene)$_n$ made from fusel oil: C, 85.63; H, 14.37. Experimental results of the elemental analysis were found to be: C, 85.53; H, 14.19.

Example 2: Oligo(pentane)$_n$ Production

Figure 4:
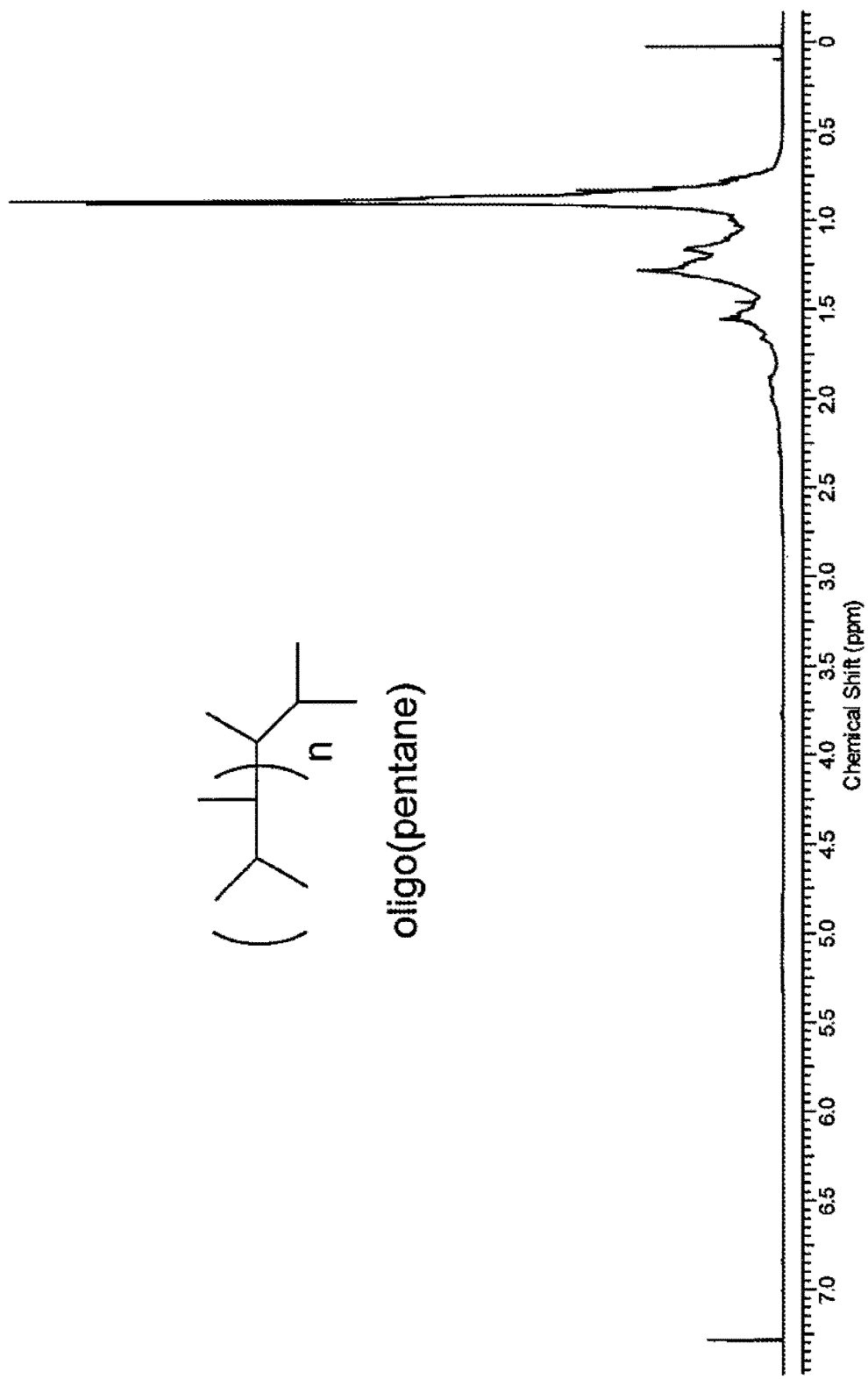
FIG. 4 is a $^1$H NMR spectrum of oligo(pentane)$_n$ produced in the method described herein.

A sample of oligo(alkene) (8.1 g) produced in Example 1 was hydrogenated in a Parr® hydrogenation apparatus (45 psi) with tetrahydrofuran (25 mL) as solvent and 10 wt % palladium on carbon (550 mg) as catalyst. The reduction was performed for 24 hours. The mixture was removed from the apparatus, filtered to remove the catalyst, and then distilled to remove the tetrahydrofuran solvent. The product produced was an oligo(pentane)$_n$. A $^1$H NMR analysis at 400 MHz was performed in deuterochloroform. The results are shown in FIG. 4. The $^1$H NMR spectra of the oligo(pentane)$_n$ in FIG. 4 shows the complete disappearance of the alkene resonances of the starting oligo(amylene)$_n$ in the range of 4.5 to 5.5 parts per million that was shown in FIG. 3.

The oligo(pentane)$_n$ was then tested to determine the net gravimetric heat of combustion. The net gravimetric heat of combustion for oligo(pentane)$_n$ was obtained using a Parr 6725 Semi-micro calorimeter outfitted with a Parr calorimeter Thermometer according to ASTM D240-17 standard test method for heat of combustion of liquid hydrocarbon fuels by bomb calorimeter. The oligo(pentane)$_n$ was found to have a net gravimetric heat of combustion of 43.946 KJ/g. In comparison, Jet A1 fuel has a net gravimetric heat of combustion of 42.8 KJ/g. Therefore, the oligo(pentane)$_n$ has an increased net gravimetric heat of combustion compared to Jet A1 fuel.

As used herein, the term "about" is used to provide flexibility to a numerical range endpoint by providing that a given value may be above or below the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Unless otherwise stated, any feature described herein can be combined with any aspect or any other feature described herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 1% v/v to about 80% v/v should be interpreted to include not only the explicitly recited limits of from about 1% v/v to about 80% v/v, but also to include individual values, such as 13% v/v, 45% v/v, 70% v/v, etc., and sub-ranges, such as from about 5% v/v to about 50% v/v, etc.

In describing and claiming the examples disclosed herein, the singular forms "a", "an", and "the" include plural referents unless the context clearly dictates otherwise.

What is claimed is:
1. A method of making a fuel comprising oligo(alkanes)$_n$, comprising:
    adding an alcohol to a reactor with a zinc dihalide salt and heating the reactor to reflux, thereby forming a mixture comprising water and oligo(alkenes)$_n$;
    removing water from the mixture using azeotropic distillation to obtain a water-lean mixture;
    distilling the water-lean mixture, thereby forming a stream comprising oligo(alkenes)$_n$ and residual alcohol, wherein n ranges from 2 to 12;
    distilling the stream comprising oligo(alkenes)$_n$ and the residual alcohol with fractionation, thereby forming a first fraction, a second fraction, a third fraction, and removing the residual alcohol, wherein:
        the first fraction includes oligo(alkenes)$_n$ with n ranging from 2 to 4;
        the second fraction includes oligo(alkenes)$_n$ with n ranging from 4 to 8; and
        the third fraction includes oligo(alkenes)$_n$ with n ranging from 8 to 12; and
    hydrogenating the first fraction, the second fraction, and the third fraction individually, thereby forming oligo(alkanes)$_n$, wherein:

the first fraction includes oligo(alkanes)$_n$ with n ranging from 2 to 4;
the second fraction includes oligo(alkanes)$_n$ with n ranging from 4 to 8; and
the third fraction includes oligo(alkanes)$_n$ with n ranging from 8 to 12.

2. The method of claim 1, wherein the alcohol is one or more aliphatic alcohols including carbons ranging from about 3 carbons to 6 carbons.

3. The method of claim 1, wherein the hydrogenating the first, second, and third fractions of the oligo(alkenes)n includes a catalyst selected from the group consisting of Ni, Pd, Pt, Ru, or combinations thereof.

4. The method of claim 1, wherein the hydrogenation occurs at a pressure ranging from about 40 psi to about 1000 psi.

5. The method of claim 1, wherein the oligo(alkanes)n with n ranging from 2 to 4 form a fuel blendstock that is blended with a second fuel selected from the group consisting of JP-8, JP-5, Jet-A, Jet-A1, F-24, Diesel #2, F-76, gasoline and combinations thereof.

6. The method of claim 5, wherein the oligo(alkanes)n with n ranging from 2 to 4 are present in the fuel blendstock in an amount ranging from about 1% v/v to about 50% v/v based on the total v/v of the fuel blendstock.

7. The method of claim 1, wherein the oligo(alkanes)n with n ranging from 4 to 8 form a fuel blendstock that is blended with a second fuel selected from the group consisting of JP-8, JP-5, Jet-A, Jet-A1, F-24, Diesel #2, F-76, gasoline and combinations thereof.

8. The method of claim 7, wherein the oligo(alkanes)n with n ranging from 4 to 8 are present in the fuel blendstock in an amount ranging from about 1% v/v to about 50% v/v based on the total v/v of the fuel blendstock.

9. The method of claim 1, wherein the oligo(alkanes)n with n from 8 to 12 form a lubricant basestock that is blended with motor oil, soap thickening greases, or hydraulic fluid in an amount ranging from about 1% v/v to about 80% v/v.

10. The method of claim 1, wherein the zinc dihalide salt is selected from the group consisting of $ZnCl_2$, $ZnBr_2$, $ZnI_2$, Zn ditriflate, and combinations thereof.

11. The method of claim 1, wherein the zinc dihalide salt is recovered from the mixture or the water-lean mixture and reused in a subsequent reaction to form more fuel.

12. The method of claim 1, wherein the hydrogenation occurs at a temperature ranging from about 20° C. to about 200° C.

13. The method of claim 1, wherein the distilling the reaction water-lean mixture produces a yield of the oligo (alkenes)n of about 25 wt %.

14. The method of claim 1, wherein the alcohol and zinc dihalide is present in a ratio of about 1:1 to about 5:1.

15. The method of claim 1, wherein the distilling the mixture is performed at a pressure ranging from about 0.1 torr to about 60 torr.

* * * * *